Figure 1:
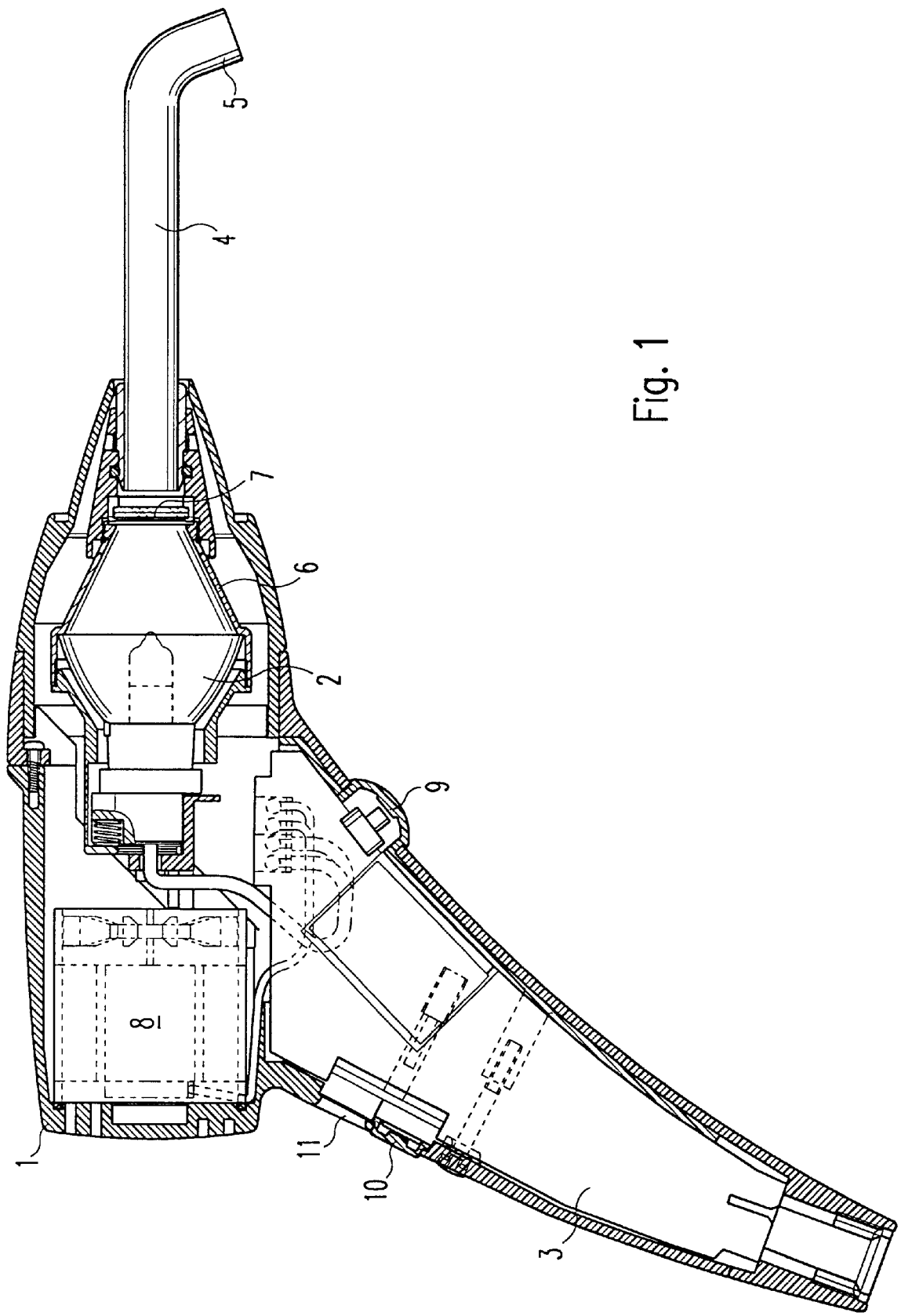

United States Patent [19]
Eibofner et al.

[11] Patent Number: 5,912,470
[45] Date of Patent: Jun. 15, 1999

[54] PROCESS AND AN APPARATUS FOR THE CURING OF LIGHT-SENSITIVE POLYMERIC COMPOSITIONS

[75] Inventors: Eugen Eibofner, Biberach; Ernst Strohmaier, Bad Schussenried, both of Germany

[73] Assignee: Kaltenbach & Voigt GmbH & Co., Biberach, Germany

[21] Appl. No.: 08/924,169

[22] Filed: Sep. 5, 1997

[30] Foreign Application Priority Data

Sep. 6, 1996 [DE] Germany ............... 196 36 266

[51] Int. Cl.⁶ ............... A61C 13/15; B29C 35/08
[52] U.S. Cl. ............... 250/504 H; 250/504 R; 250/492.1; 433/29
[58] Field of Search ............... 250/504 H, 504 R, 250/492.1; 433/29

[56] References Cited

U.S. PATENT DOCUMENTS 4,276,479  6/1981  Mibu et al. ............... 250/492.1
4,450,139  5/1984  Bussiere et al. ............... 250/504 H
5,634,711  6/1997  Kennedy et al. ............... 433/29

FOREIGN PATENT DOCUMENTS

| 0 003 312 | 8/1979 | European Pat. Off. . |
| 0 037 461 | 10/1981 | European Pat. Off. . |
| 2 348 227 | 11/1977 | France . |
| 2 629 999 | 10/1989 | France . |
| 3 411 994 A1 | 10/1985 | Germany . |
| 90 17 070 U | 5/1992 | Germany . |
| WO 95/07731 | 3/1995 | WIPO . |

*Primary Examiner*—Jack I. Berman
*Attorney, Agent, or Firm*—Scully, Scott, Murphy & Presser

[57] ABSTRACT

In a process for the curing of light-sensitive polymeric compositions by irradiation with light of wavelength suited to the polymeric composition it is proposed that the irradiation be carried out with a light intensity increasing continuously or in stepped form. An apparatus for carrying out said process is further proposed in which the raising of the light intensity is controlled during an irradiation procedure by a control unit (13).

12 Claims, 4 Drawing Sheets

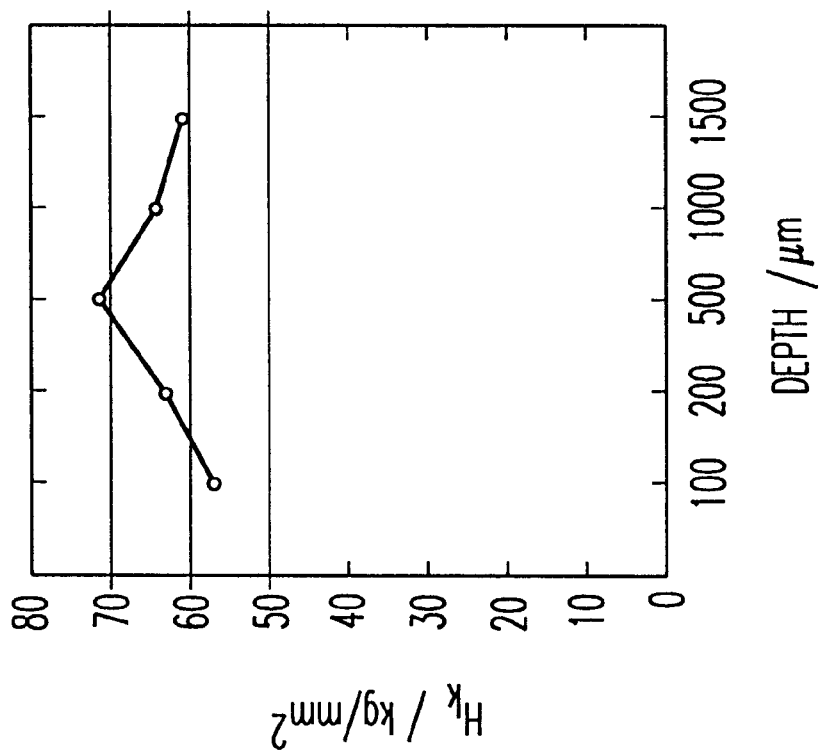
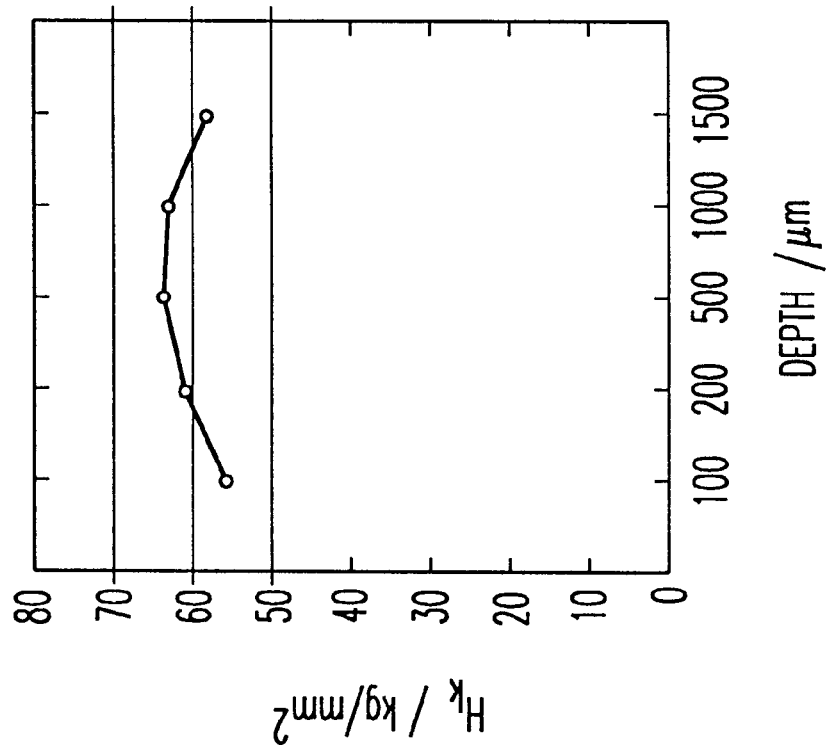

PROCESS AND AN APPARATUS FOR THE CURING OF LIGHT-SENSITIVE POLYMERIC COMPOSITIONS

The invention relates to a process for the curing of light-sensitive polymeric compositions according to the preamble of claim 1, as well as an apparatus for carrying out said process according to the preamble of claim 9.

Light-sensitive polymeric compositions of the kind discussed here are used, for example, in dentistry to make fillings, bonds, seals or similar. The plastics composites employed in dentistry can as a rule be cured or polymerised by an irradiation with light of a wavelength of some 400 to 550 nm.

In addition to dental treatment directly on the patient, such a process can also, for example, be applied at the laboratory level for the processing of dental prostheses, dentures or similar. The process is in principle applicable whenever a light-sensitive polymeric composition is to be cured by means of photo-polymerisation.

An apparatus for carrying out the photo-polymerisation procedure mentioned at the beginning is disclosed in German utility model DE-GM 90 17 070.9. An adjustable light emission apparatus, in particular for the curing of light-sensitive dental materials, is described there, which contains a light source and an optical light guide system. In order to keep the light intensity of the light emission apparatus constant at defined values, the apparatus comprises a detector for measuring the light intensity and a control unit for keeping the light intensity constant.

There are further presented in a company brochure (Demetron-Programm) of the company KERR GmbH, Karlsruhe, on pages 4–6, various light polymerisation units. The manual units contain a halogen lamp with a maximum output in the wavelength range of 400 to 525 nm, a permanent cooling, a detachable, sterilizable light guide and a preselector switch for curing times of up to 60 seconds or a continuous operating cycle.

Further polymerisation units are contained in a company brochure of the company DENTLSPLY DeTrey, Constance. The manual units of this company brochure, which form the preamble of the apparatus claim, contain in addition to the conventional components, namely light source for 400–500 m, optical light guide system, cooling device and filter, a microprocessor for controlling constant light intensity and an input unit for inputting of the irradiation time by the user together with a display unit for displaying the irradiation time set.

In the above-mentioned prior art the photo-polymerisation takes place at constant light intensity and fixed wavelength, and only the irradiation time, i.e. the curing time, is varied. Tests have shown that if the plastics composites used in practice are irradiated with a relatively high light intensity for a relatively short irradiation time, as is conventional according to the general prior art, firstly the curing takes place irregularly, in particular deeper areas are cured to a lesser extent, and secondly the still pasty plastics material shrinks. This produces in the plastics material an irregular bonding of the plastics particles with one another and with the sides of a cavity, resulting in a reduction in the quality and the life of e.g. fillings.

The aim of the invention is to create a process and a suitable apparatus for carrying out the process, which eliminates the above-mentioned disadvantage and produces a more regular photo-polymerisation of the plastics material.

This object is achieved by a process mentioned at the beginning with the distinguishing features of claim 1. By the continuous or stepped raising of the light output during the irradiation process a more intensive and more regular curing is achieved with simultaneously less shrinkage of the plastics material, which leads to a better bonding of the plastics particles to one another and to the sides of a cavity.

The object is further achieved by an apparatus with the features of claim 9. The control unit of the apparatus according to the invention permits a continuous or stepped raising of the light output during an irradiation procedure, so that the process according to the invention can be carried out problem-free.

As a development of the invention the user can choose by means of an input unit between different irradiation modes, namely between an irradiation with constant light intensity or with light intensity increasing continuously or in stepped form.

The irradiation mode selected can further be displayed in a display unit together with the irradiation time set or remaining.

With advantage the user can with the aid of a pilot light beam align the light beam for the irradiation onto the area to be cured prior to the actual irradiation procedure. If a light beam of reduced light intensity is used as the pilot light beam, the latter can also be used for a manually controllable, extremely slowly commencing curing.

Further developments of the invention are the subject-matter of further sub-claims.

There will be described below, by means of the attached drawing, an embodiment of an apparatus according to the invention and the process that can be carried out with it.

Figure 2:
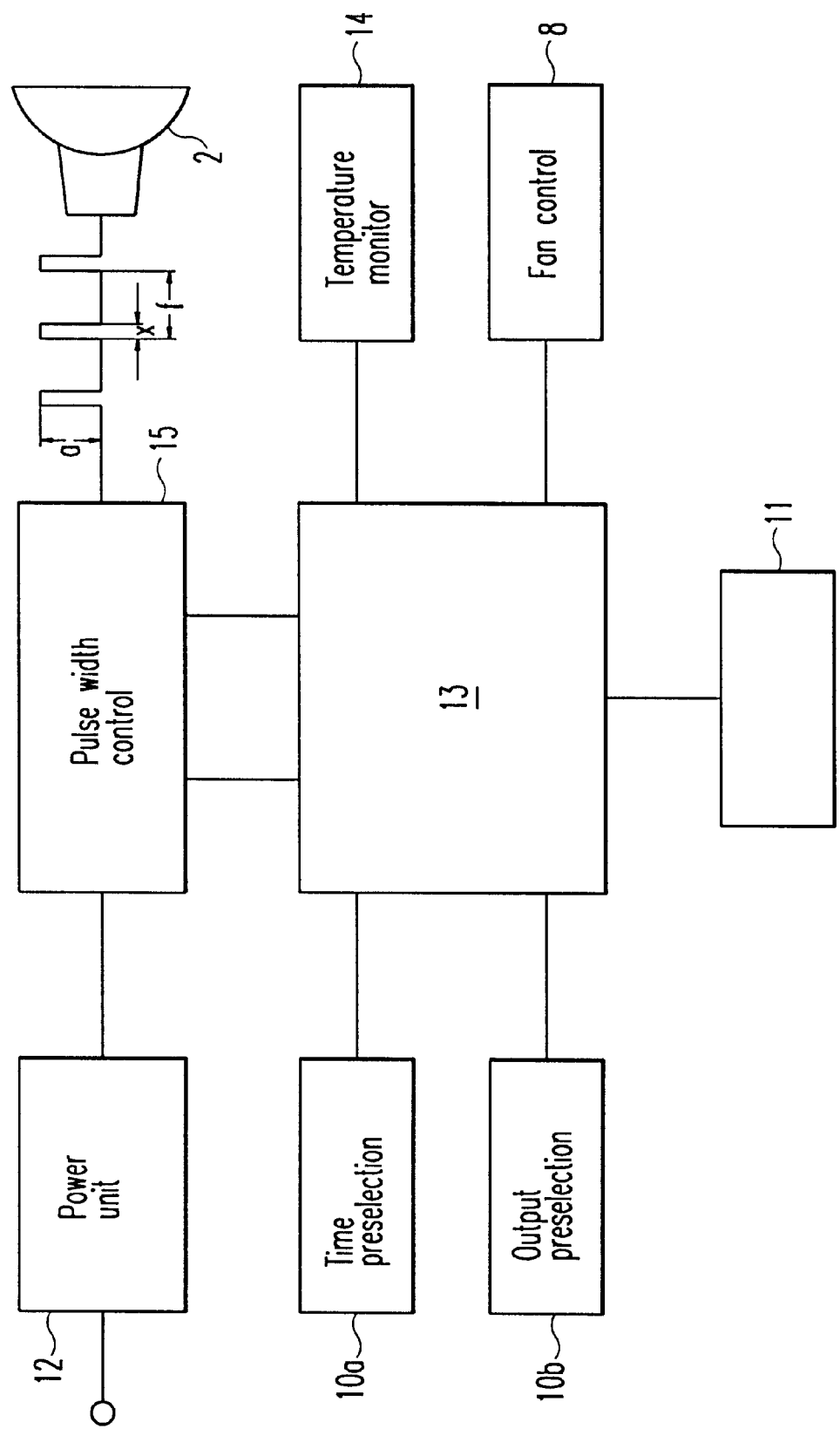
Figure 3:
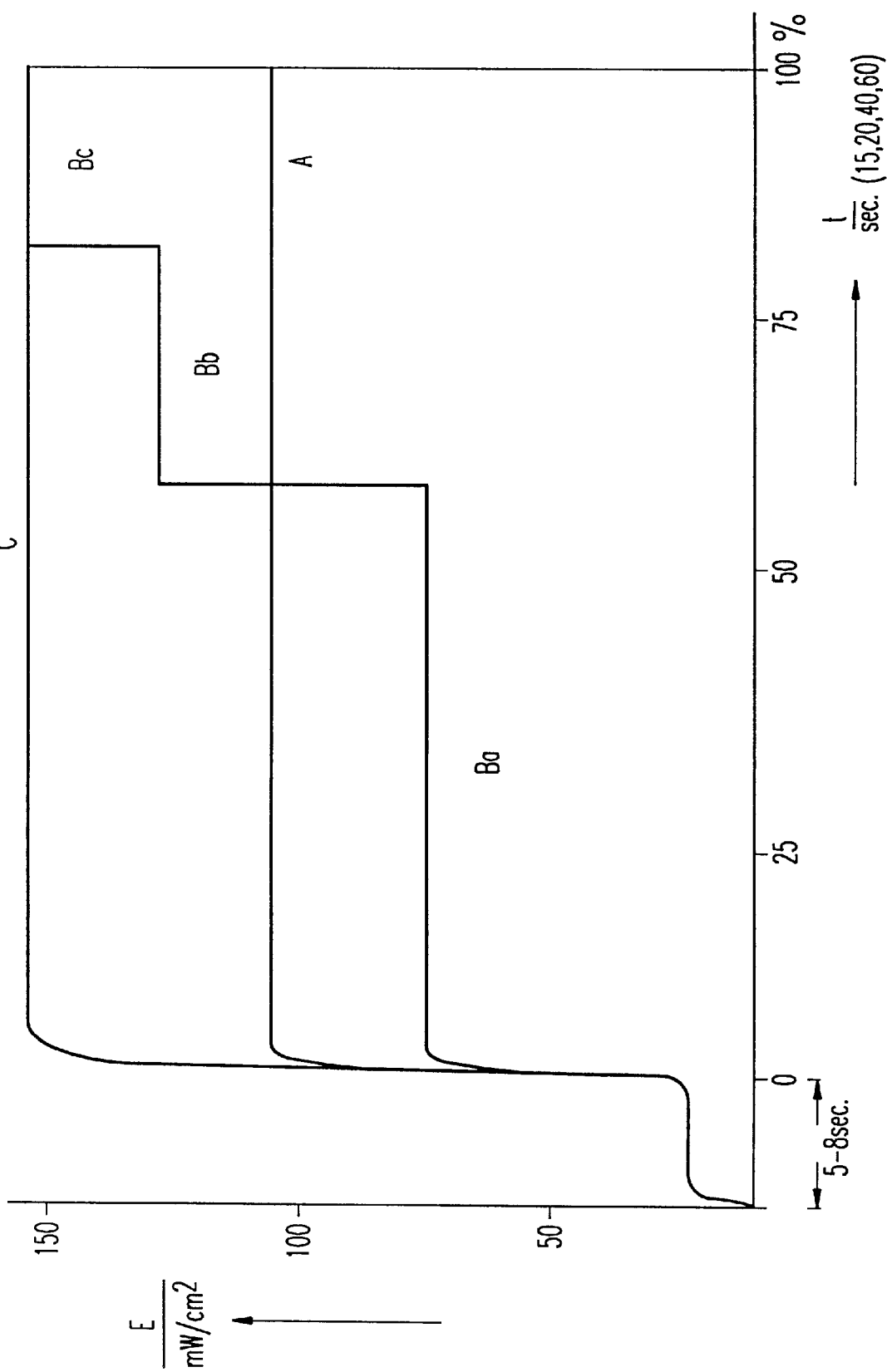

FIG. 1 shows a photo-polymerization unit according to the invention in cross-section;

FIG. 2 a block diagram of the electronic circuit of the photo-polymerization unit according to FIG. 1;

FIG. 3 a light intensity-time chart illustrating the various irradiation modes of the photo-polymerization unit; and FIG. 4 two charts comparing the polymerization results according to a conventional process and that according to the invention.

FIG. 1 shows a photo-polymerization unit according to the invention as a manual unit, which can be used in particular in the dental sector. The manual unit consists essentially of a case 1 with light source 2 contained therein, a handle 3 and an optical light guide system 4. One end of the optical light guide system 4 is correspondingly opposite the light source 2 and the other end 5 is formed for the emission of light and curved slightly. The light guide can be a glass tube or be filled with conventional light guide material, such as for example fibres of glass, quartz or plastics material.

There is preferably used as the light source 2 an incandescent halogen lamp with an integral reflector 6. The light emitted by the incandescent halogen lamp 2 is guided by the reflector 6 through a filter system 7 and focussed onto the incident surface of the optical light guide system 4. The filter system 7 also incorporates conventionally a spectral filter, which is transparent only to light of the preferred wavelength range of some 400 to 550 nm, in which a polymerization of the plastics materials mostly used takes place, but a narrower or even different wavelength range can in principle also be filtered out depending on the material to be cured. Behind the incandescent halogen lamp 2 a fan 8 is arranged in the case 1 as a cooling device, in order to prevent overheating of the lamp 2 and the unit, in particular with longer operating times.

On the handle 3 is located a switch 9 for switching on the light source 2. The switching off of the light source 2 switched on by pressing of the switch 9 can be effected in various ways. The light source 2 is switched off either by a timing element on expiration of a particular time or by renewed pressing of the switch 9 or by release of the switch 9 held in position since the switching on. The end of the irradiation procedure is preferably notified to the user by an acoustic signal.

In addition the handle 3 comprises an input unit 10 and a display unit 11. There can be inputted by the user via the input unit 10 both the desired irradiation time and the irradiation mode. The user can read off from the display unit 11 the irradiation time set or remaining and the irradiation mode set.

Further details of the photo-polymerization unit shown in FIG. 1 will now be explained by means of the block diagram of FIG. 2.

For the supply of energy there is located in the manual unit a power pack 12, which is connected to an external mains supply via a cable or which comprises batteries or accumulators. The central component of the electronic circuit of the photo-polymerization unit is a control unit 13. The control unit 13 is connected to the input unit 10 and receives from the latter the data inputted by the user for the time pre-selection 10a and for the output or mode pre-selection 10b. The user data 10a, b inputted via the input unit 10 are displayed on the display unit 11. The control unit 13 controls by means of the user data 10a, b inputted via the input unit 10 and the data predetermined by the works the light intensity of the light source 2 and the irradiation time. The irradiation takes place as a rule in pulse form with an amplitude a, a pulse width x and a pulse repetition frequency f, the latter being set by a control member 15 connected to the control unit 13.

In order to monitor the actual light intensity emitted by the lamp 2, a detector for measuring the light intensity can additionally be accommodated in the apparatus, which is coupled to the control unit 13 in such a way that the control unit 13 can adjust the light intensity to a constant value according to the user data 10b set.

The irradiation time is controlled on the basis of the time pre-selection 10a; the user has in general a choice here between continuous operation (switching on and off controlled only by the switch 9) and a particular, finite irradiation time, which he can input continuously or select from preset values. The conventional irradiation times of the photo-polymerization units discussed here lie between 10 and 60 seconds.

The wavelength of the irradiation and the light intensity in the various irradiation modes are conventionally set by the works. The user can however for example choose between three different irradiation modes A, B and C, which are shown in FIG. 3 in the form of a light intensity-time chart. The time t is plotted in % of the total irradiation time towards the right in FIG. 3 and the light intensity E in $mW/cm^2$ towards the top.

The chart in FIG. 3 shows the light intensity curves of three irradiation modes A, B and C selected as examples for a total irradiation time of 15, 20, 40 and 60 seconds respectively. The first irradiation mode A produces an irradiation with constant low light intensity of some 100 $mW/cm^3$ and the third irradiation mode C produces an irradiation with constant high light intensity of some 150 $mW/cm^3$.

Curve B shows a stepped raising of the light intensity in the second irradiation mode, which produces a photo-polymerization according to the process according to the invention. The first stage Ba of the irradiation takes place in general at some 30–60% of the maximum light intensity of the third stage Bc for up to some 75% of the total irradiation time. The second stage Bb of the irradiation takes place in general at some 50–90% of the maximum light intensity of the third stage Bc for some 30% of the total irradiation time. The remainder of the irradiation takes place in the third stage Bc with maximum light intensity.

In addition to the three-stage raising of the light intensity represented here, a raising with a different number of irradiation stages or else a continuous increasing of the light intensity during the irradiation procedure is also possible in principle. The irradiation modes A, B and C specified in this embodiment, in particular mode B according to the invention, as well as the characteristic data for light intensity and irradiation time, have nevertheless proved to be particularly advantageous in tests on conventional light-sensitive plastics materials used in dentistry. These settings can however naturally be adapted to other materials which may possibly be used in the future.

The irradiation mode A, B or C selected is indicated in the display unit together with the irradiation time set or remaining. The distinguishing of the modes in the display can be effected for example by a continuously luminous dot for mode A, a flashing dot for mode B and a non-existent dot for mode C in addition to the displayed irradiation time.

Prior to the irradiation in one of the available irradiation modes A, B or C the optical light guide system 4 is first of all aligned optimally onto the desired curing area. This takes place by means of a so-called pilot light beam.

The pilot light beam can for example originate from an additional light source on the manual unit and consist of a closely bundled light beam, such as a laser light beam, for example. Alternatively the pilot light beam can also be produced more simply by some 5 to 10%, preferably some 8%, of the maximum light intensity of the existing light source 2.

If the switch 9 on the manual unit is kept pressed at the start of the treatment procedure, the light intensity remains constant at the reduced value. In so doing no dazzling or damage to the eyes of the patient can furthermore occur. The user of the manual unit can then with the aid of the pilot light beam produced align the optical light guide system 4 optimally onto the curing area. If the switch 9 is released again, the pre-selected irradiation mode is executed automatically. The time of the alignment can also be limited to some 5 to 8 seconds, and the control unit 13 then be switched automatically to the light intensity of the corresponding irradiation mode. In this case an additional acoustic notification on completion of the alignment mode or at the start of the irradiation mode is advisable.

The end of the irradiation procedure is with advantage likewise notified to the user by an acoustic signal.

An extremely slowly commencing curing can also be effected by means of the alignment mode with reduced light intensity. The user can control this manually by keeping the switch 9 pressed.

The alignment of the optical light guide system or an extremely slowly commencing curing with the pilot light beam of reduced light intensity is shown on the left in FIG. 3 from the time t=0 on the axis of the irradiation time t for the three irradiation modes A, B and C. The light intensity comes to some 5 to 10% of the maximum light intensity for some 5 to 8 seconds.

In FIG. 2 there are connected to the control unit 13, as further components of the electronic circuit, also a monitoring 14 of the temperature, in particular the temperature of the light source 2, and a triggering of the cooling device 8 according to the measured temperature in the case 1 or the light source 2.

In FIG. 4 the photo-polymerization results from two samples which were produced according to a conventional process (FIG. 4b) and the process according to the invention (FIG. 4a) are contrasted for comparison purposes.

To produce the samples, the filling material (Brilliant Lux, Colténe, Altstätten, colour: brown) was introduced into standardized holes (diameter: 4 mm, depth: 1.9±0.1 mm) in Plexiglas and polymerized with an apparatus described above and then post-cured for 10 days in a drying oven (T=37° C.). The samples were then embedded in cold-polymerizing synthetic resin and after complete curing of the resin cut vertically through the centre of the filling with a diamond disc with glycerol cooling. The samples were then embedded with the cut surface facing upwards in plane-parallel steel rings and polished to a high lustre in several polishing stages.

The recording of the polymerization of the plastics samples took place by means of a hardness test according to Knoop. At each measurement the diamond used for the measurement acted on the surface with a force of 100 pond for 30 seconds. The Knoop micro-hardness $H_K$ was measured on several samples at distances of 50 µm, 100 µm, 200 µm, 500 µm, 1000 µm and 1500 µm from the surface respectively.

FIGS. 4a and 4b show in each case towards the right the depth or the distance from the surface of the sample in µm and towards the top the Knoop micro-hardness $H_K$ in kg/mm² as a measure of the degree of polymerization of the sample.

FIG. 4b shows the result of the hardness measurement on a sample which was irradiated with a light intensity of some 140 mW/cm² for some 20 seconds. Clear differences in the degree of polymerization achieved at varying distances from the surface are discerned, with a maximum distance in the hardness of some 15 kg/mm². The differences in the curing are further intensified at greater light intensities than that used here.

The results of the hardness measurements on a sample which was irradiated by the process according to the invention in three stages of some 78 mW/cm² for 20 seconds, 110 mW/cm² for 10 seconds and 140 mW/cm² for 10 seconds are shown in FIG. 4a. The curve of FIG. 4a shows a distinctly more regular shape over the entire depth than that of the curve of FIG. 4b. The maximum hardness difference comes in this case to only some 8 kg/mm², i.e. approximately half compared with the conventional process.

Even if in FIG. 4b according to the conventional method a greater maximum hardness is achieved at a depth of some 500 µm than with the process according to the invention, it should be emphasized that the regularity of the polymerization is of greater importance for the quality of the cured plastics material.

Irradiation mode B with stepped or else continuous raising of the light intensity represents an improvement on the conventional irradiation method with high light intensity and short irradiation time, and it achieves a distinctly better quality of the cured plastics material with just as short an irradiation time. A similar result could also be achieved with lower light intensities than before if there is a willingness to accept substantially longer irradiation times.

The above description of the process according to the invention is geared to the dentistry sector by means of an exemplifying embodiment of a corresponding apparatus. The process can furthermore be applied both directly to the patient for dental treatment and at the laboratory level as preparation for dental treatment or for test purposes. It is in addition also possible to apply the process outside dentistry; in principle whenever a light-sensitive polymeric composition is to be cured by means of photo-polymerization. Wavelength ranges, light intensities and irradiation times other than those in the embodiment described above then have to be selected, in accordance with the particular application.

We claim:

1. An apparatus for carrying out a process for the curing of light-sensitive polymeric compositions with a light source, an optical light guide system, a control unit for controlling the irradiation time, an input unit for the inputting of the irradiation time by the user, a display unit for displaying the irradiation time set and/or remaining, a control unit for controlling the light output delivered by the light source, a cooling device for cooling the light source and a filter system, wherein the light intensity delivered by the light source is increasable continuously or in stepped form by the control unit during an irradiation procedure.

2. An apparatus as claimed in claim 1, wherein the light intensity delivered by the light source is increasable by the control unit in three stages directly succeeding one another, wherein the irradiation time of the first stage is up to some 75%, that of the second stage some 30% and that of the third stage the remaining time of the total irradiation period.

3. An apparatus as claimed in claim 1, wherein the light intensity delivered by the light source is increasable by the control unit in three stages directly succeeding one another, wherein the light intensity of the first stage is some 30–60% and that of the second stage some 50–90% of the maximum light intensity of the third stage.

4. An apparatus as claimed in claim 3, wherein the maximum light intensity of the third stage is some 130 to 200 mW/cm².

5. An apparatus as claimed in claim 1, wherein the spectral filter is transparent to a wavelength of 400 to 550 nm.

6. An apparatus as claimed in claim 1, wherein the control unit makes irradiation in different, predetermined irradiation modes possible.

7. An apparatus as claimed in claim 6, wherein the control unit makes irradiation in three different modes possible, namely a first mode with constant low light intensity, a second mode with light intensity increased continuously or in stepped form and a third mode with constant high light intensity.

8. An apparatus as claimed in claim 6, wherein the apparatus comprises an input unit for the selection of the irradiation mode by the user.

9. An apparatus as claimed in claim 6, wherein the apparatus comprises a display unit for displaying the irradiation mode set by the user.

10. An apparatus as claimed in claim 1, wherein the apparatus comprises a detector coupled to the light rays, which measures the light intensity and supplies a corresponding electrical signal to said control unit which for its part keeps the light intensity to the level set by said control unit according to the measuring signal received.

11. An apparatus as claimed in claim 1, wherein the apparatus comprises a further light source for a pilot light beam for aligning the light beam emitted by the light source.

12. An apparatus as claimed in claim 1, wherein the light intensity delivered by the light source is controllable by the control unit prior to the irradiation procedure to some 5 to 10% of the maximum light intensity.

* * * * *